United States Patent
Dubournet et al.

(10) Patent No.: US 11,414,714 B2
(45) Date of Patent: Aug. 16, 2022

(54) METHODS AND KITS FOR THE DETECTION OF POWDERY MILDEW

(71) Applicant: Bayer SAS, Lyons (FR)

(72) Inventors: Patrice Dubournet, Francheville (FR); Semcheddine Cherrad, Tassin La Demi Lune (FR); Sébastien Vacher, Limonest (FR)

(73) Assignee: Bayer SAS, Lyons (FR)

( * ) Notice: Subject to any disclaimer, the term of this patent is extended or adjusted under 35 U.S.C. 154(b) by 396 days.

(21) Appl. No.: 15/743,220

(22) PCT Filed: Jul. 8, 2016

(86) PCT No.: PCT/EP2016/066338
§ 371 (c)(1),
(2) Date: Jan. 9, 2018

(87) PCT Pub. No.: WO2017/009251
PCT Pub. Date: Jan. 19, 2017

(65) Prior Publication Data
US 2018/0202008 A1      Jul. 19, 2018

(30) Foreign Application Priority Data

Jul. 10, 2015  (EP) .................................... 15290182

(51) Int. Cl.
*C12Q 1/6895*   (2018.01)
*C12Q 1/686*    (2018.01)

(52) U.S. Cl.
CPC .......... *C12Q 1/6895* (2013.01); *C12Q 1/686* (2013.01); *C12Q 2545/114* (2013.01)

(58) Field of Classification Search
None
See application file for complete search history.

(56) References Cited

U.S. PATENT DOCUMENTS

| | | | |
|---|---|---|---|
| 2004/0023207 A1* | 2/2004 | Polansky | A61K 31/00 435/5 |
| 2008/0182252 A1* | 7/2008 | Antovich | C12Q 2545/101 435/6.12 |
| 2012/0100546 A1* | 4/2012 | Lowery, Jr. | C12Q 1/689 435/6.15 |

OTHER PUBLICATIONS

GenBank Accession No. GQ255473 [online] Sep. 9, 2010 [retrieved on Oct. 19, 2019] retrieved from https://www.ncbi.nlm.nih.gov/nuccore/gq255473 (Year: 2010).*

Costadone, L. Development and Evaluation of Detection-based Air Sampling Programs for Grapevine Powdery Mildew. Dissertation , Washington State University (pp. i-x, 1-38). (Year: 2009).*

Falacy et al. Detection of Erysiphe necator in Air Samples Using the Polymerase Chain Reaction and Species-Specific Primers. Phytopathology 97(10):1290-1297. (Year: 2007).*

Mishra et al. High Throughput Detection of PCR Products and SNPs for Molecular Breeding, in: Molecular Plant Breeding: Principle, Method and Application. Singh et al, eds. Studium Press LLC; pp. 79-96. (Year: 2008).*

Arya et al. Basic principles of real-time quantitative PCR. Expert Review of Molecular Diagnostics 5(2):209-219. (Year: 2005).*

Saenz et al. Phylogeny of the *Erysiphales* (powdery mildews) inferred from internal transcribed spacer ribosomal DNA sequences. Can. J. Bot. 77:150-168. (Year: 1999).*

* cited by examiner

*Primary Examiner* — Samuel C Woolwine
(74) *Attorney, Agent, or Firm* — Morrison & Foerster LLP

(57) ABSTRACT

The present invention relates to means, methods and kits for the specific detection of the causing agent of powdery mildew on grapes, the fungus *Erysiphe necator*. More specifically, the methods according to the invention are quantitative methods based on quantitative Polymerase Chain Reaction.

13 Claims, No Drawings

Specification includes a Sequence Listing.

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
gacagagtga cgctcgtgat                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
ttcagcgggt attcctacct                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3 gtggcccta aagacagtgg                                                20
```

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
ctgtcgcgag gaacaagtta                                               20

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct

<400> SEQUENCE: 5
tcactctgtc gcgaggaac                                                19

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
cacctttgtc cggtcatccg g                                             21

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
ctacgcgtag agcccacgcg                                               20

<210> SEQ ID NO 8
<211> LENGTH: 10
<212> TYPE: DNA
<213> ORGANISM: Artificial Sequence
<220> FEATURE:
<223> OTHER INFORMATION: Synthetic Construct

<400> SEQUENCE: 8
tcactctgtc                                                          10

<210> SEQ ID NO 9
<211> LENGTH: 11
<212> TYPE: DNA
<213> ORGANISM: Artificial Sequence
<220> FEATURE:
<223> OTHER INFORMATION: Synthetic Construct

<400> SEQUENCE: 9
cgtagagccc a                                                        11

METHODS AND KITS FOR THE DETECTION OF POWDERY MILDEW

CROSS REFERENCE TO RELATED APPLICATIONS

This application is a National Phase application under 35 U.S.C. § 371 of International Application No. PCT/EP2016/066338, filed Jul. 8, 2016, which claims priority benefit of European Application No. 15290182.3, filed Jul. 10, 2015.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052018800SEQLIST.txt, date recorded: Jan. 9, 2018, size: 3 KB).

The present invention relates to methods and kits for the detection of the causing agent of powdery mildew on grapes, the fungus *Erysiphe necator*. More specifically, the methods according to the invention are quantitative methods based on quantitative Polymerase Chain Reaction.

BACKGROUND

Grapevine powdery mildew caused by *Erysiphe necator* (also known as *Uncinula necator*) is one of the most widespread diseases of grapevine (*Vitis vinifera* L.) worldwide. *Erysiphe necator* belong to the ascomycetes and is an obligate biotrophic fungus, i.e. its growth and reproduction are fully dependent on its living grapevine host (grapes and leaves). As a consequence, grapevine powdery mildew cannot be cultured in vitro, is difficult to cryo-conserve, and a reliable transformation protocol has not been established as yet, posing serious challenges for using it experimentally in laboratories (Spanu et al., 2012, *New Phytologist* 195: 20-22).

In spite of their importance, molecular characterization of vineyards powdery mildews and genetic databases information remain poor. Aside from *Blumeria graminis*, only 23 expressed sequence tags (ESTs) have been deposited at GenBank for the Erysiphales (National Center for Biotechnology Information, 2009). A major contributing factor to this absence of expression data for powdery mildew is the difficulty to isolate and maintain the fungus in laboratory in-vitro culture (Cadle-Davidson et al., 2010, *J. Phytopathol.* 158: 69-71). Nonetheless, recently works on genome sequencing of *E. necator* fungus provided some putative genes information and NCBI research today give more than 500 ESTs.

In vineyard, the monitoring of disease symptoms is a crucial component of an integrated approach to vineyard management and the production of disease-free grapes. However, visual assessment of powdery mildew is highly subjective, particularly when infection of leaves is slight.

The aim of the present invention is to provide a molecular quantitative PCR method for improved management of powdery mildew infection in field, preferably for early detection of *Erysiphe necator* DNA on grapevine leaves before appearance of visual symptoms. Such molecular diagnostic method can be a very helpful tool in the management and planning of fungicide treatments.

Previous attempts have been made to try detecting *Erysiphe necator* by qPCR, in particular for detecting and monitoring resistant populations, by e.g. designing qPCR primers targeting the CYP51 gene (Dufour et al., 2011, *Pest Manag Sci* 67: 60-69; Jones et al., 2014, BMC Genomics 15:1081).

DESCRIPTION OF THE INVENTION

The present invention provides methods and means for detecting or assaying the presence of the fungus *Erysiphe necator* in samples, in particular in samples of grapevine, and more particularly for quantitatively measuring the level of presence of the fungus *Erysiphe necator* on grapevine. One advantage of the invention lies in the sensitivity of the method, possibly enabling the detection of the fungus before any symptoms become visible on the plants.

The method according to the invention makes use of the quantitative Polymerase Chain Reaction (PCR) technology, also known as qPCR or real-time PCR. PCR is the technology allowing the rapid amplification of target DNA sequences using specific oligonucleotides as primers of amplification reactions which take place in repeated cycles. This technology is well known and understood to the person skilled in the art. Classical PCR allows the qualitative detection of certain target DNA sequences, whereas qPCR allows a quantitative measure of the amount of the target DNA sequence.

Like classical PCR, qPCR requires a set of two oligonucleotides which are used as primers of the amplification reaction. The primers are specific to the target DNA sequence to be amplified, i.e. they consist of short nucleic acid fragments corresponding to portions of the target DNA sequence, preferably portions immediately flanking the target DNA sequence. One primer is the forward primer and the other is the reverse primer, each matching, i.e. being identical in sequence to, a portion of DNA sequence flanking the target DNA sequence, and thus defining the target DNA sequence to be amplified, which is the DNA sequence located between (though including) the two primers. The forward primer is the oligonucleotide matching the sense strand of the portion of DNA sequence at one end of the target DNA sequence, and the reverse primer is the oligonucleotide matching the complementary (antisense) strand of the portion of DNA sequence at the other end of the target DNA sequence. During each cycle of the PCR, the DNA sequence containing the target DNA sequence denaturates (unpairs) under high temperatures (about 95° C.) thereby generating single-stranded DNA to which the primers can hybridize under a following step of lower temperatures (about 65° C.), then enabling heat-tolerant DNA Polymerases to extend the synthesis of the target DNA sequence from each primers. The repetition of this thermal cycle (about 30 times) allows the generation of thousands of copies of the target DNA sequence, which can then be identified in e.g. an agarose gel electrophoresis.

qPCR is also named real-time or quantitative PCR because, in addition to classical PCR, the reaction also incorporates fluorescent reporter compounds, allowing the detection and measure of the amount of target DNA formed at each cycle. Fluorescent reporter compounds can be specific to the PCR-amplified target DNA sequence (specific oligonucleotide probe on which a fluorescent reporter is linked, together with a quencher), or unspecific (fluorescent dye binding to double-stranded DNA, like e.g. the SYBR Green dye). Further comparison of the measured fluorescence with appropriate references enables the precise quantification of the initial quantity of target DNA, e.g. in a sample.

The important element in qPCR for assaying the presence and quantity of a given pathogen in a certain sample, e.g. a plant or soil sample, is the preliminary identification of a pair of primers that are specific to the pathogen to be assayed. Primers specific to a given pathogen are primers which allow the amplification of a target DNA sequence which is specific to the pathogen, i.e. which is only present in the pathogen of interest and not, or not exactly, in e.g. a different pathogen species.

According to the present invention, the primers are specific to the fungus *Erysiphe necator*, i.e. they allow the amplification of a portion of the DNA of this fungal species which is only present in this fungal species and not in other, even closely related, species. Only with specific primers can the qPCR method be able to discriminate between all DNA sequences from diverse organisms that might be present in e.g. a leaf or soil sample.

According to a specific embodiment, the invention therefore provides for oligonucleotide primers selected from the group consisting of the oligonucleotides comprising the nucleotide sequences SEQ ID NO: 1, SEQ ID NO: 3, SEQ ID NO: 4, and SEQ ID NO: 5. The invention also encompasses the oligonucleotide primers selected from the group consisting of the oligonucleotides comprising a nucleotide sequence complementary to the nucleotide sequences SEQ ID NO: 1, SEQ ID NO: 3, SEQ ID NO: 4 and SEQ ID NO: 5.

Preferred embodiments of the invention are oligonucleotide primers selected from the group consisting of the oligonucleotides having the nucleotide sequences SEQ ID NO: 1, SEQ ID NO: 3, SEQ ID NO: 4, and SEQ ID NO: 5; or oligonucleotide primers selected from the group consisting of the oligonucleotides having a nucleotide sequence complementary to the nucleotide sequences SEQ ID NO: 1, SEQ ID NO: 3, SEQ ID NO: 4 and SEQ ID NO: 5.

An oligonucleotide is a short molecule of DNA, generally made of at least 10 nucleotides, and up to 30 nucleotides. An optimal oligonucleotide, to be used as a PCR primer or as a probe, is usually made of 18 to 24 nucleotides, but shorter or longer oligonucleotides may be used, and the skilled artisan knows which parameters to consider for selecting oligonucleotides of appropriate length for a given purpose. An oligonucleotide according to the invention is preferably made of 19 to 21 nucleotides.

The invention therefore also encompasses oligonucleotides primers comprising a nucleotide sequence of at least 10 contiguous nucleotides of the oligonucleotides having the nucleotide sequences SEQ ID NO: 1, SEQ ID NO: 2, SEQ ID NO: 3, SEQ ID NO: 4, and SEQ ID NO: 5; or at least 10 contiguous nucleotides of the oligonucleotides having a nucleotide sequence complementary to the nucleotide sequences SEQ ID NO: 1, SEQ ID NO: 2, SEQ ID NO: 3, SEQ ID NO: 4 and SEQ ID NO: 5, with the exception of (a) the specific oligonucleotide having the nucleotide sequence of SEQ ID NO:2 and (b) the specific oligonucleotide having the nucleotide sequence tcactctgtc.

Contiguous nucleotides refer to a series of nucleotides of a DNA molecule or an oligonucleotide which are consecutive to one another in the nucleotide sequence of such DNA molecule or oligonucleotide.

According to certain alternative embodiments, the oligonucleotide primers have a length of at least 11, 12, 13, 14, 15, 16, 17, 18, 19, 20, 21, 22, 23, 24, 25, 26, 27, 28, 29 or 30 contiguous nucleotides. More specifically, the oligonucleotide primers have a length of 11, 12, 13, 14, 15, 16, 17, 18, 19, 20, 21, 22, 23, 24, 25, 26, 27, 28, 29 or 30 contiguous nucleotides.

As used herein, "complementary" nucleotide sequences refers to two nucleotide sequences which nucleotide bases are complementary over a certain contiguous part of their respective sequences according to the standard Watson & Crick complementarity rules, and are therefore capable of pairing or hybridizing with each other over their respective complementary parts. Specifically, purine bases are pairing with pyrimidines bases, and more specifically a guanine base pairs with a cytosine base (G:C) and an adenine base pairs with either a thymine base (A:T) in the case of DNA, or with a uracil base (A:U) in the case of RNA.

An oligonucleotide primer is an oligonucleotide that is used as primer in a PCR amplification process (a qPCR in the context of the present invention). Accordingly, an oligonucleotide primer is an oligonucleotide matching, i.e. identical in sequence to, a portion of a target DNA intended to be amplified in the PCR process. When the PCR process is run so that the two strands of the target DNA unpair, the oligonucleotide primer binds to the portion of the target DNA to which it is complementary in sequence. Once the oligonucleotide primer is bound, it can then be used as starting point for a DNA Polymerase to initiate amplification of the target DNA.

The oligonucleotide primers of the invention are specific to a portion of DNA of the genome of the fungus *Erysiphe necator*. More specifically, these oligonucleotide primers are specific to the nuclear ribosomal Internal Transcribed Spacers (ITS) of *Erysiphe necator*. ITS are two non-coding DNA regions (named ITS1 and ITS2) present in all eukaryotes and located between the two genes encoding the small-subunit (18S) ribosomal RNA and the large-subunit (25S or 28S) ribosomal RNA, more specifically respectively between the gene encoding the small-subunit (18S) ribosomal RNA and the one encoding the 5.8S ribosomal RNA for ITS1, and between the gene encoding the 5.8S ribosomal RNA and the one encoding the and the large-subunit (25S or 28S) ribosomal RNA for ITS2.

Any PCR amplification process, including qPCR, uses at least two oligonucleotide primers, usually referred to as a pair of oligonucleotide primers. A pair of oligonucleotide primers consists of one oligonucleotide primer named the forward oligonucleotide primer, and one oligonucleotide primer named the reverse oligonucleotide primer. The forward and the reverse oligonucleotide primers are respectively located at each end of the target DNA to be amplified in the PCR process. The forward oligonucleotide primer is identical in sequence to the portion of the sense strand corresponding to its end of the target DNA, and therefore binds to the complementary (i.e. antisense) strand of the target DNA during the PCR process, whereas the reverse oligonucleotide primer is identical in sequence to the portion of the antisense strand corresponding to its end of the target DNA (at the other end of the target DNA), and therefore binds to the complementary (i.e. sense) strand of the target DNA during the PCR process. A pair of oligonucleotide primers therefore consists of two oligonucleotide primers, one forward oligonucleotide primer and one reverse oligonucleotide primers, together defining, and necessary for, a target DNA to be amplified in a PCR process.

Preferably, the invention therefore provides for a pair of oligonucleotide primers selected from the group consisting of (i) the pair of oligonucleotides having the nucleotide sequences SEQ ID NO: 1 for the forward oligonucleotide primer and SEQ ID NO: 2 for the reverse oligonucleotide primer, (ii) the pair of oligonucleotides having the nucleotide sequences SEQ ID NO: 3 for the forward oligonucleotide primer and SEQ ID NO: 4 for the reverse oligonucleotide primer, and (iii) the pair of oligonucleotides having the nucleotide sequences SEQ ID NO:3 for the forward oligonucleotide primer and SEQ ID NO: 5 for the reverse oligonucleotide primer.

Alternatively, the invention also provides for a pair of oligonucleotide primers selected from the group consisting of (i) the pair of oligonucleotides having the nucleotide sequences complementary to the nucleotide sequences SEQ ID NO: 1 for the reverse oligonucleotide primer and SEQ ID NO: 2 for the forward oligonucleotide primer, (ii) the pair of oligonucleotides having the nucleotide sequences complementary to the nucleotide sequences SEQ ID NO: 3 for the reverse oligonucleotide primer and SEQ ID NO: 4 for the forward oligonucleotide primer, and (iii) the pair of oligonucleotides having the nucleotide sequences complementary to the nucleotide sequences SEQ ID NO:3 for the reverse oligonucleotide primer and SEQ ID NO: 5 for the forward oligonucleotide primer.

The invention also encompasses the pairs of oligonucleotides consisting of oligonucleotides comprising at least 10 contiguous nucleotides of the nucleotide sequences of the above oligonucleotides.

A preferred pair of oligonucleotide primers for carrying out the invention is the pair of oligonucleotides comprising at least 10 contiguous nucleotides of the nucleotide sequences SEQ ID NO: 1 for the forward oligonucleotide primer and SEQ ID NO:2 for the reverse oligonucleotide primer; or alternatively the pair of oligonucleotides comprising at least 10 contiguous nucleotides complementary to the nucleotide sequences SEQ ID NO: 1 for the reverse oligonucleotide primer and SEQ ID NO:2 for the forward oligonucleotide primer.

Preferably, the pair of oligonucleotide primers consists of the oligonucleotides having the nucleotide sequences SEQ ID NO: 1 for the forward oligonucleotide primer and SEQ ID NO:2 for the reverse oligonucleotide primer; or alternatively the oligonucleotides having the nucleotide sequences complementary to SEQ ID NO: 1 for the reverse oligonucleotide primer and SEQ ID NO:2 for the forward oligonucleotide primer The use of the pairs of oligonucleotide primers allows the specific amplification of the ITS region of the fungus *Erysiphe necator* in qPCR.

The invention also provides for oligonucleotides to be used as probes for specifically detecting, and measuring the quantity of, target DNA amplified during the qPCR process. The oligonucleotide probes according to the invention are selected from the oligonucleotides comprising at least 10 contiguous nucleotides of the nucleotide sequences SEQ ID NO: 6 and SEQ ID NO: 7; or from the oligonucleotides comprising at least 10 contiguous nucleotides of the sequences complementary to the nucleotide sequences SEQ ID NO: 6 and SEQ ID NO: 7, with the exception of the specific oligonucleotide having the nucleotide sequence cgtagagccca.

A preferred oligonucleotide to be used as probe for carrying out a qPCR according to the invention is the oligonucleotide comprising at least 10 contiguous nucleotides of the nucleotide sequence SEQ ID NO: 6. Alternatively, a preferred oligonucleotide to be used as probe for carrying out a qPCR according to the invention is the oligonucleotide comprising at least 10 contiguous nucleotides complementary to the nucleotide sequence SEQ ID NO: 6.

Oligonucleotides used as probes that are designed based on the nucleotide sequence of SEQ ID NO: 6 are to be used with the pair of oligonucleotides used as primers that are designed based on the nucleotide sequences of SEQ ID NO: 1 and 2. This combination of oligonucleotide primers and probe are preferred to carry out a qPCR according to the invention.

Alternatively, oligonucleotides used as probes that are designed based on the nucleotide sequence of SEQ ID NO: 7 are to be used either with the pair of oligonucleotides used as primers that are designed based on the nucleotide sequences of SEQ ID NO: 3 and 4; or with the pair of oligonucleotides used as primers that are designed based on the nucleotide sequences of SEQ ID NO: 3 and 5.

The oligonucleotides provided in the present invention, used as primer or as probe, have a length of at least 10 contiguous nucleotides. According to certain alternative embodiments, the oligonucleotides have a length of 11, 12, 13, 14, 15, 16, 17, 18, 19, 20, 21, 22, 23, 24, 25, 26, 2 7, 28, 29 or 30 nucleotides. Preferably, the oligonucleotides of the invention have a length of 19 to 21 nucleotides.

The invention therefore also provides for a method for the specific detection of the fungus *Erysiphe necator*, comprising:

(a) subjecting a sample to quantitative polymerase chain reaction (qPCR) using a pair of oligonucleotide primers of the invention; and
(b) determining the presence, or absence, of *Erysiphe necator* in the sample by visualizing, or not, the target DNA amplified by the qPCR.

The "specific detection" means that the method aims at specifically detecting the fungus *Erysiphe necator*, and no other living organism, in samples that may also contain other living organisms. At least, the method according to the invention aims at not detecting any living organisms that may be present in a sample collected in places susceptible of containing *Erysiphe necator*, i.e. samples collected on or around plant species of the genus *Vitis*, more particularly *Vitis vinifera*.

A "sample" according to the invention preferably refers to a small amount of material collected in places where *Erysiphe necator* is susceptible of being present, but can in principle be collected anywhere. Since *Erysiphe necator* has species of the genus *Vitis* as its preferred host plants, a preferred place where this fungus is susceptible of being present is either on plant species of the genus *Vitis*, or a place where such plant species grow, e.g. the surrounding soil. Since one of such host plant species of *Erysiphe necator* is the widely cultivated vineyard *Vitis vinifera*, a preferred place where the fungus is susceptible of being present is either on plants of the species *Vitis vinifera*, e.g. on leaves, grapes, trunk (or arms), or stems (canes), or a place where such plant species grow, e.g. the surrounding soil. A preferred sample according to the invention is therefore either a small amount of leaves (such as e.g. a leaf disc cut from a whole leaf) or grape of plants of the species *Vitis vinifera*, or a small amount of soil surrounding the place where plants of the species *Vitis vinifera* are growing. A sample according to the invention can also be collected from the upper or lower surface of leaves, of from the surface of grapes, trunk (or arms), or stems (canes), i.e. without collecting plant material, by appropriate means known to the skilled artisan.

In order for the qPCR to possibly amplify any target DNA present in the sample, the DNA from any living matter present in the sample, including *Erysiphe necator* spores or any other biological structure, needs to be made freely accessible to the different elements of the qPCR (i.e. primers, DNA Polymerase, fluorescent reporters). Accordingly, the sample subjected to qPCR may be used as such, or may previously be subjected to a step of DNA extraction. When a prior DNA extraction is performed on the sample, the skilled artisan may use any DNA extraction method known in the art.

The invention also relates to a method for the specific quantification of the fungus *Erysiphe necator*, comprising: (a) subjecting a sample to quantitative polymerase chain reaction (qPCR) using a pair of oligonucleotide primers of the invention; and
(b) determining the quantity of *Erysiphe necator* in the sample by comparing the measured quantity of target DNA amplified by the qPCR with reference DNA amplification data.

The "specific quantification" means that the method aims at specifically quantifying the amount of the fungus *Erysiphe necator*, and no other living organism, present in samples that may also contain other living organisms.

The quantity of *Erysiphe necator* present in the sample is determined according to the method of the invention, first by measuring the quantity of target DNA amplified by the qPCR, and then by comparing such measured quantity of target DNA amplified by the qPCR with some reference DNA amplification data. "Reference DNA amplification data" consist of standard data corresponding to predetermined measures of the quantities of target DNA amplified by the qPCR, after a defined number of amplification cycles, from known initial quantities of target DNA. Based on such reference DNA amplification data, it is possible to infer from the measured quantity of target DNA amplified by the qPCR in a sample, which quantity of such target DNA (hence of the fungus *Erysiphe necator*) was present in the sample before the qPCR amplification process.

The determination and measure of the target DNA during the qPCR process is made with either with the oligonucleotide probes according to the invention or with any reporter as hereinafter described.

The invention further provides for a diagnostic kit used for detecting the fungus *Erysiphe necator*, whereby the kit comprises either at least one of the oligonucleotide primers selected from the group consisting of the oligonucleotides comprising at least 10 contiguous nucleotides of the nucleotide sequences SEQ ID NO: 1, SEQ ID NO: 2, SEQ ID NO: 3, SEQ ID NO: 4, and SEQ ID NO: 5; or at least one of the oligonucleotide primers selected from the group consisting of the oligonucleotides comprising at least 10 contiguous nucleotides complementary to those of SEQ ID NO: 1, SEQ ID NO: 2, SEQ ID NO: 3, SEQ ID NO: 4 and SEQ ID NO: 5.

Preferably, the diagnostic kit used for detecting the fungus *Erysiphe necator* comprises the pair of oligonucleotide primers selected from the group consisting of the pairs of oligonucleotides each comprising at least 10 contiguous nucleotides of the nucleotide sequences SEQ ID NO: 1 for the forward oligonucleotide primer and SEQ ID NO: 2 for the reverse oligonucleotide primer, SEQ ID NO: 3 for the forward oligonucleotide primer and SEQ ID NO: 4 for the reverse oligonucleotide primer, and SEQ ID NO:3 for the forward oligonucleotide primer and SEQ ID NO: 5 for the reverse oligonucleotide primer.

Alternatively, the diagnostic kit used for detecting the fungus *Erysiphe necator* comprises the pair of oligonucleotide primers selected from the group consisting of the pairs of oligonucleotides each comprising at least 10 contiguous nucleotides complementary to the nucleotide sequences SEQ ID NO: 1 for the reverse oligonucleotide primer and SEQ ID NO: 2 for the forward oligonucleotide primer, SEQ ID NO: 3 for the reverse oligonucleotide primer and SEQ ID NO: 4 for the forward oligonucleotide primer, and SEQ ID NO:3 for the reverse oligonucleotide primer and SEQ ID NO: 5 for the forward oligonucleotide primer.

Most preferably, the diagnostic kit used for detecting the fungus *Erysiphe necator* comprises the pair of oligonucleotide primers comprising at least 10 contiguous nucleotides of the nucleotide sequences SEQ ID NO: 1 for the forward oligonucleotide primer and SEQ ID NO:2 for the reverse oligonucleotide primer; or alternatively the pair of oligonucleotide primers comprising at least 10 contiguous nucleotides complementary to the nucleotide sequences SEQ ID NO: 1 for the reverse oligonucleotide primer and SEQ ID NO:2 for the forward oligonucleotide primer.

According to a specific embodiment, the diagnostic kit comprises the pair of oligonucleotide primers consisting of the oligonucleotides having the nucleotide sequences SEQ ID NO: 1 for the forward oligonucleotide primer and SEQ ID NO:2 for the reverse oligonucleotide primer; or alternatively the oligonucleotides having the nucleotide sequences complementary to SEQ ID NO: 1 for the reverse oligonucleotide primer and SEQ ID NO:2 for the forward oligonucleotide primer.

In addition to the oligonucleotide primers, the kit also contains a reporter, preferably a fluorescent reporter. A reporter is a compound binding to the DNA amplified during the qPCR, thereby enabling the measurement of the quantity of DNA amplified. A fluorescent reporter is a compound, e.g. a fluorophore, emitting a specific fluorescent light when exited by a light at a wavelength specific to the compound.

For the purpose of the kit and methods according to the invention, the reporter may be a non-specific dye that intercalates in double-stranded DNA molecules. These dyes increase their fluorescent signal when bound to double-stranded nucleic acid and may be detected by a standard fluorescence detection system. Any such DNA-intercalating dye known to the skilled artisan, such as e.g. ethidium bromide or SYBR Green may be suitable for carrying out the invention. A preferred non-specific DNA-intercalating fluorescent dye for carrying out the invention is the SYBR Green dye, also known with its IUPAC name as N',N'-dimethyl-N-[4-[(E)-(3-methyl-1,3-benzothiazol-2-ylidene)methyl]-1-phenylquinolin-1-ium-2-yl]-N-propylpropane-1,3-diamine.

Alternatively to a non-specific DNA-intercalating dye, the fluorescent reporter of the kit according to the invention may be a sequence-specific fluorescent probe. Such a probe is an oligonucleotide labelled with a fluorophore. When used for qPCR purposes, such labelled oligonucleotide probes have a sequence complementary to at least 10 contiguous nucleotides of the target sequence which is amplified by the qPCR.

A preferred probe for carrying out the invention is a probe labelled according to the TaqMan system. The TaqMan system is a technology available from the manufacturer Life Technologies Inc. According to the TaqMan system, the oligonucleotide probe designed specifically to hybridize with the amplified target DNA is covalently attached with a fluorophore in its 5'-end and with a quencher in its 3'-end. Examples of suitable fluorophores for use in the TaqMan system include 6 carboxy-fluorescein (FAM) or tetrachlorofluorescein (TET). A typical quencher is the tetramethylrhodamine (TAMRA). The principle of this TaqMan system is that the quencher inhibits fluorescence by the fluorophore as long as they both are in the close proximity on the probe. Once the oligonucleotide probe hybridizes with the target DNA during the qPCR amplification process, it becomes degrades by the Taq Polymerase as this enzyme elongates the oligonucleotide primers along the DNA corresponding to the target DNA. This degradation releases the fluorophore and the quencher, which becomes no longer in close proximity with the fluorophore, thereby enabling the fluorophore to emit its fluorescence, which can then be detected and measured by appropriate means usually integrated in qPCR devices (i.e. thermocyclers).

A preferred oligonucleotide probe to be used in the kit for being labelled with the TaqMan system, or with any other system known to be suitable to the skilled artisan, is an oligonucleotide selected from the oligonucleotides comprising at least 10 contiguous nucleotides of the nucleotide sequences SEQ ID NO: 6 and SEQ ID NO: 7; or from the oligonucleotides comprising at least 10 contiguous nucleotides of the sequences complementary to the nucleotide sequences SEQ ID NO: 6 and SEQ ID NO: 7.

A preferred oligonucleotide to be used as probe for carrying out a qPCR according to the invention is the oligonucleotide comprising at least 10 contiguous nucleotides of the nucleotide sequence SEQ ID NO: 6. Alternatively, a preferred oligonucleotide to be used as probe for carrying out a qPCR according to the invention is the oligonucleotide comprising at least 10 contiguous nucleotides complementary to the nucleotide sequence SEQ ID NO: 6.

Oligonucleotides used as probes in the kit, that are designed based on the nucleotide sequence of SEQ ID NO: 6 are to be used with the pair of oligonucleotides used as primers that are designed based on the nucleotide sequences of SEQ ID NO: 1 and 2. This combination of oligonucleotide primers and probe are preferred to use in the kit and to carry out a qPCR according to the invention.

Alternatively, oligonucleotides used as probes that are designed based on the nucleotide sequence of SEQ ID NO: 7 are to be used either with the pair of oligonucleotides used as primers that are designed based on the nucleotide sequences of SEQ ID NO: 3 and 4; or with the pair of oligonucleotides used as primers that are designed based on the nucleotide sequences of SEQ ID NO: 3 and 5.

The oligonucleotides provided for the kit according to the present invention preferably have a length of at least 10 contiguous nucleotides. According to certain alternative embodiments, the oligonucleotides have a length of 11, 12, 13, 14, 15, 16, 17, 18, 19, 20 or 21 nucleotides.

The kit may further include elements, such as reagents, necessary to carry out the qPCR, as known to the skilled artisan. In addition to the pair of primers and a probe, the kit may comprise one or more enzymes (Taq polymerase) or reagents to be utilized in the qPCR reactions. Enzymes may be present in lyophilized form or in appropriate buffers. Furthermore, the kit may contain all of the additional elements necessary to carry out a qPCR, such as buffers, extraction reagents, enzymes, pipettes, plates, nucleic acids, nucleoside triphosphates, filter paper, gel materials, transfer materials, autoradiography supplies, instructions and the like.

Sequence Listing:
SEQ ID NO: 1: primer ITS-F
SEQ ID NO: 2: primer ITS-R
SEQ ID NO: 3: primer ITS A-F
SEQ ID NO: 4: primer ITS A-R
SEQ ID NO: 5: primer ITS A-R1
SEQ ID NO: 6: ITS-Fprobe
SEQ ID NO: 7: ITS-A-Rprobe The various aspects of the invention will be understood more fully by means of the experimental examples below.

All the methods or operations described below are given by way of example and correspond to a choice, made among the various methods available for achieving the same result. This choice has no effect on the quality of the result, and, consequently, any appropriate method can be used by those skilled in the art to achieve the same result. In particular, and unless otherwise specified in the examples, all the recombinant DNA techniques employed are carried out according to the standard protocols described in Sambrook and Russel (2001, Molecular cloning: A laboratory manual, Third edition, Cold Spring Harbor Laboratory Press, NY) in Ausubel et al. (1994, Current Protocols in Molecular Biology, Current protocols, USA, Volumes 1 and 2), and in Brown (1998, Molecular Biology LabFax, Second edition, Academic Press, UK). Standard materials and methods for plant molecular biology are described in Croy R.D.D. (1993, Plant Molecular Biology LabFax, BIOS Scientific Publications Ltd (UK) and Blackwell Scientific Publications (UK)). Standard materials and methods for PCR (Polymerase Chain Reaction) are also described in Dieffenbach and Dveksler (1995, PCR Primer: A laboratory manual, Cold Spring Harbor Laboratory Press, NY) and in McPherson et al. (2000, PCR—Basics: From background to bench, First edition, Springer Verlag, Germany).

EXAMPLES

Example 1: Design of Primers Specific to *Erysiphe necator*

Several powdery mildew isolates were used to develop the qPCR method. They were purified and maintained on detached leaves of *Vitis Vinifera* cv. Cinsaut. Bioassay inoculations occurred with blowing spores from 12-14-day-old sporulating leaves onto the upper surface of disinfected leaves by an air pump in Plexiglas settling tower. Infected leaves were incubated at 22° C. in a growth chamber (12/12 h light/dark photoperiod) and were transferred to fresh agar medium every 3 to 4 days. Fungal material growing on the leaf surfaces was scraped into Eppendorf tubes and contaminated leave disc were frozen at −20° C.

DNA was extracted from *Erysiphe necator* fungal isolates according to NucleoSpin® plantII kit (Macherey-Nagel) following the manufacturer's instructions. DNA extracts were stored at −20° C.

ITS region of three laboratories *Erysiphe necator* isolates were PCR amplified and sequenced using ITS1 and ITS4 primers (White, T. J. et al. (1990), PCR Protocols: a Guide to Methods and Applications 18, 315-322). All PCR amplifications were performed in 25 µl reaction mixture including 10 µl GoTaq Mix (Promega, France), 400 pmol of each primer and 30 ng of template DNA. The PCR cycle was programmed in a Eppendorf thermocycler as follows: 94° C. for 10 min and then 30 cycles at 94° C. for 1 min, 58° C. annealing temperature for 1 min, 72° C. for 1 min, then a final extension of 72° C. for 10 min. Amplified products were subjected to electrophoresis (TBE 0.5×) in 1.5% agarose gel, detected with SYBR® Safe and photographed under UV light.

ITS amplified PCR products were sequenced for the three tested *Erysiphe necator* isolates. Obtained sequences were compared by alignment software to sequences published in NCBI database (GenBank accession no. AF049332.1 and AF011325.1).

Multiple sequences of internal transcribed spacer amplified from different isolates of *E. necator* fungus are available in database. PCR amplification with primers ITS1 and ITS4 of ITS region on DNA extracted from pure mycelium isolates or on total necrotic foliar discs DNA give the same result. A sequence of about 600 nucleotides was obtained from the three tested isolates (Annexe 1). Analysis of this sequence with the ClustalW multiple sequence alignment software (http://www.ebi.ac.uk/Tools/msa/clustalw2) shows similarities between published sequences and sequence of the three isolates tested in laboratory.

Primers were designed for qPCR development in conserved and aligned regions between the different isolates. The probe and primer sets designed are shown in Table 1.

TABLE 1 primers and probes tested for *E. necator* qPCR

| | | Tm |
|---|---|---|
| Set-I-: Amplicon Size = 67 | | |
| ITS_A-F | 5'-GTGGCCCTTAAAGACAGTGG-3' (SEQ ID NO: 3) | 59.59 |
| ITS_A-R | 5'-CTGTCGCGAGGAACAAGTTA-3' (SEQ ID NO: 4) | 59.07 |
| ITS_A-Rprobe | 5'FAM-CTACGCGTAGAGCCCACGCG-3'TAMRA (SEQ ID NO: 7) | 68.38 |
| Set-IA-: Amplicon Size = 72 | | |
| ITS_A-F | 5'-GTGGCCCTTAAAGACAGTGG-3' (SEQ ID NO: 3) | 59.59 |
| ITS_A-R1 | 5'-TCACTCTGTCGCGAGGAAC-3' (SEQ ID NO: 4) | 59.42 |
| ITS_A-Rprobe | 5'FAM-CTACGCGTAGAGCCCACGCG-3'TAMRA (SEQ ID NO: 7) | 68.38 |
| Set-II-: Amplicon Size = 97 | | |
| ITS-F | 5'-GACAGAGTGACGCTCGTGAT-3' (SEQ ID NO: 1) | 59.00 |
| ITS-R | 5'-TTCAGCGGGTATTCCTACCT-3' (SEQ ID NO: 2) | 58.67 |
| ITS-Fprobe | 5'FAM-CACCTTTGTCCGGTCATCCGG-3'TAMRA (SEQ ID NO: 6) | 69.02 |

All qPCRs performed contained a forward primer, a reverse primer, and either a probe using 6-carboxyfluorescein (FAM) as a reporter fluorophore on the 5'end, with N,N,N_,N_tetramethyl-6-carboxyrhodamine (TAMRA) as a quencher on the 3'end (Table 1), or a non-specific reporter (e.g. SYBR Green). qPCR twofold concentrated master mix (Platinium MasterMix SybrGreen-Invitrogen and probe MasterMix-Roche), 300 nM probe, and 300 nM of each primer were combined in sterile, nuclease-free water (Invitrogen) prior to addition of any DNA template. The vial containing the master mix was vortexed to ensure homogeneity of the solution and briefly spun down in a microcentrifuge. Aliquots (15 µl) of the reaction mix were dispensed to each 20 µl glass capillary (Roche, France). Two reporter systems were tested, the intercalating SYBR Green essay and the TaqMan probe system.

Template DNA (5 µl) was added to each reaction, and the capillaries were sealed with plastic cap. The LightCycler 2.0 Sample Carousel was centrifuged before qPCR analysis. Three sets of primers or primers/probe were tested in capillary LightCycler (Roche applied science) system with different running programs (Table 1). All assays were identical in probe and primer concentrations. Only primer set and corresponding program giving high qPCR efficiency (90 to 100%) and specific amplification was selected for in-vivo experiments.

Standard curve was generated from amplification of the target gene (DNA-plasmid) present at a range of initial template concentrations, and then the Ct values for each template concentration are determined. Subsequently, a simple linear regression of these Ct values is plotted against the log of the initial gene copy number. For each experiment, amplification efficiency (E), the linear regression coefficient (r2) and especially the y-intercept value describes the standard curve and indicates the sensitivity of the reaction. The slope of the standard curve gives the efficiency of the PCR reaction by the following equations: Efficiency=10(−1/slope)−1.

qPCR Efficiency and Specificity

To select the best set of primers listed in Table 1, plasmid DNA containing the ITS region sequence of *E. necator* was serially diluted in 1:10 ratios. Copy numbers of the cloned ITS sequences were derived from the molecular weight of the cloning vector and insert. qPCR analysis was performed on plasmid concentrations using the different primer sets with SYBRGreen or primers coupled to additional TaqMan hydrolysis probe system. A characteristic marker for high quality assays is the PCR amplification efficiency. Evaluation of efficiency is essential for every qPCR gene quantification procedure. The optimal qPCR amplification efficiency was obtained with primers ITS-Forward (5'-GACAGAGTGACGCTCGTGAT-3'(SEQ ID NO: 1)) and ITS-Reverse (5'-TTCAGCGGGTATTCCTACCT-3'(SEQ ID NO. 2)) (Set-II) with SYBRGreen as fluorophore. Quantification was performed using the following amplification parameters: initial preheating at 95° C. for 15 min, followed by 40 cycles of denaturation at 95° C. for 30 s, annealing at 60° C. for 60 s, extension at 72° C. for 20 s. An additional melting curve analysis involved a 15 s pre-melting at 95° C. followed by a temperature ramp from 60° C. to 95° C., with a 15 s hold at each 0.1° C. step of the ramp. Data acquisition and analysis was acquired according to second derivative maximum method.

Calculated efficiency of qPCR analysis with this set of primers (Set-II) is close to 100% while other tested primers shows low efficiency and higher ΔCp discard between one dilution to the next. SYBR Green detection gives more sensibility than TaqMan probe system and we observed 3 cycles difference between the two tested systems for the same higher plasmid-DNA concentration (1.2×106 gene copy). Repeating plasmid-DNA standard curve runs with selected primers set and program reveal qPCR assay stability and robustness.

Because SYBR Green is non-specific and binds to any double-stranded DNA, it is essential to use primer pairs that are highly specific to their target sequence. To ensure that the qPCR method developed using these primers is highly specific to the *E. necator* target gene, genomic DNA of other fungus was tested. 100 ng of DNA extracted from mycelium of *Botrytis cinerea*, *Alternaria solani*, *Cladosporium* spp., *Penicillium* spp., *Verticilium* spp., *Fusarium solani* and *Stachybotrys chartarum* was analysed by qPCR with the selected primers (Set-II). All tested fungus were either not detected or detected with higher Ct values and out-of-range of the most diluted template DNA (120 gene copies) of standard curve. As in practice, qPCR analysis should be performed on total DNA extracted from leaves, these result shows that qPCR method is specific to *E. necator* fungus and the presence of other contaminating fungus does not interfere in powdery mildew quantification on leaves.

Example 2: In-Vivo Quantification of *Erysiphe necator* DNA on Grapevine Leaves

To validate sensibility and accuracy of the method on biological samples, qPCR analysis was applied on total extracted DNA from foliar discs contaminated with serial dilution of *E. necator* spores in laboratory bioassays. Total DNA was extracted on 4 foliar discs and 100 ng DNA was analyzed with qPCR analysis method for each spore concentration tested at different incubation periods.

The number of *E. necator* target gene was determined from plasmid-DNA standard curve. The lowest concentration of 2 spores/cm$^2$, tested immediately after spraying (d+0) was detected at Ct=27.13 cycles equivalent to $9.4 \times 10^2$ gene copy. Interestingly, qPCR quantification of other tested spore concentrations shows that number of gene copy increase proportionally with number of *E. necator* spores on leaf surface. The highest spores concentration tested (C4=175 spores/cm$^2$) was detected at Ct=21.98 cycles corresponding to $3.5 \times 10^4$ gene copy. Almost all foliar discs incubated in adequate growth conditions of powdery mildew show increase of *E. necator* target gene quantified in samples. These results confirm correlation between DNA amount analyzed by qPCR method and biomass evolution of fungus on leaves estimated by visual annotations. Amount of *E. necator* DNA measured by qPCR analysis reach $1.3 \times 10^6$ gene copy after 12 days incubation of foliar discs infected with spores concentrated at 175 spores/cm$^2$.

Therefore, use of qPCR analysis method allows us to detect and quantify specifically DNA of *E. necator* spores at earlier stage on grapevine leaves even before germination and apparition of visual symptoms. Sensibility of the method in biological essays makes it able to detect spores presence on leaves as low as 2 spores/cm$^2$.

Example 3: Assessment of *E. necator* DNA by qPCR Analysis in Field Contamination In order to validate the qPCR method in field conditions, artificial contamination was conducted in grapevine parcels at different dates with different densities of inoculums prepared in laboratory.

Assays were conducted in French vineyard St Martin d'Armagnac (Gros Manseng) from April to August 2013. Planted vineyard parcels with 10 plants were tested with an adjacent non-inoculated 5 plants parcel. Leaves were contaminated with spraying *E. necator* spore solutions at different concentrations: C1 (0.1 spore/cm$^2$), C2 (1 spore/cm$^2$) and C3 (10 spores/cm$^2$). Artificial inoculation of powdery mildew spores were performed at three different dates: 18 April, 7 May and 23 May. For each condition, 5 leaves were collected at d+0, d+7, d+14 and d+30 days after contamination for qPCR analysis.

The five leaves were sampled for each tested condition and pooled foliar discs were prepared from these leaves. Total DNA was extracted and 100 ng was analyzed by qPCR. Therefore, qPCR data expresses amount of *E. necator* DNA in five leaves per sample.

Analysis of leaves collected from Gros Manseng grapevine parcels for the first inoculation date (23 Apr. 2013) show presence of *E. necator* DNA ($1.1 \times 10^3$ gene copy) only in samples corresponding to leaves infected with spore's concentrations C2 (1 spore/cm$^2$) and C3 (10 spores/cm$^2$) when collected immediately after contamination (d+0). Target DNA was also amplified ($4.2 \times 10^3$ gene copy) in total DNA extracted from leaves contaminated with C3 (10 spores/cm$^2$) and collected at d+14. *E. necator* DNA was not detected in the other samples tested.

For the second inoculation date (7 May 2013), significant amplification was observed in leaves infected with the three tested concentrations of *E. necator* spores and collected at d+0 ($1.03 \times 10^3$ gene copies for C1, $1.1 \times 10^3$ gene copies for C2 and $1.03 \times 10^3$ gene copies for C3). Leaves collected after 30 days of artificial test contamination showed presence of *E. necator* DNA at $9.93 \times 10^3$ and $2.38 \times 10^3$ gene copies for C2 (1 spore/cm$^2$) and C3 (10 spores/cm$^2$) respectively. In all samples collected for contaminated date 23 May 2013, only leaves tested with C2 (1 spore/cm$^2$) and immediately collected (d+0) detected *E. necator* DNA.

These results show that *E. necator* DNA is detectable when the fungus develops on the plants.

Example 4: Artificial and Natural Field Contamination 2014: qPCR Analysis and Powdery Mildew Progress In order to further assess the qPCR method, other tests were performed in 2014 on two artificially-contaminated assays and four natural assays in different regions. For every sample in natural assay, 10 leaves were collected. In contrast, 5 leaves were collected in artificial contaminated test for each spore concentration sprayed (C1=0.1 spores/cm$^2$, C2=1 spores/cm$^2$ and C3=10 spores/cm$^2$). 4 foliar discs were analyzed per leaf for both assays. In artificially-contaminated assay named "14 00 06-EN" conducted in 9 Apr. 2014, *E. necator* was detected at d+0 (corresponding to fresh collected leaves) in 5 leaves out of 15 collected leaves, 4 of these leaves having been contaminated with the highest tested concentration C3 and 1 leaf with concentration C1. Half of the collected leaves after 7 days (d+7) and 14 days (d+14) contain *E. necator*. From leaves sample analyzed after 30 days (d+30), 6 leaves were tested positively to *E. necator*. In other tested dates, powdery mildew was detected on leaves at different proportion. Ratio of leaves containing *E. necator* at d+0 vary between 2 (test conducted 23 Apr. 2014) to 6 leaves (test conducted 07 may 2014) out of 15 collected leaves for the three tested concentrations.

At the same time, monitoring was also conducted in 4 grapevines without any introduction of *E. necator* spores. In this case, 10 leaves were collected at different stages and sent to the laboratory for qPCR analysis. For test "14 00 08 EN-B", qPCR analysis detected *E. necator* DNA in leaves collected at Date 2 (30 Apr. 2014) and Date 3 (13 May 2015) but not at Date 1 (17 Apr. 2014). Frequency of leaves naturally contaminated by powdery mildew differed between tested areas (Zone 1, Zone 2 and Zone 3). In leaves collected from Zone 1, *E. necator* DNA was highly present in 9 out of 10 leaves collected. At the same time, visual annotation was performed in grapevine and no powdery mildew symptoms were visually observed at this stage. *E. necator* necrosis began to appear only 15 days later (first visual annotation 22 May 2014).

qPCR analysis of leaves collected in the other monitoring tests showed *E. necator* DNA presence on few leaves only at D1 (23 Apr. 2014), but no powdery mildew was detected in leaves at the two other dates tested (05 and 19 May 2014). Same data was obtained with another test, where only 2 leaves were identified to contain *E. necator* DNA for D1 (22 Apr. 2014) and no infection detected by qPCR on leaves collected at D2 (5 May 2014) and D3 (2 Jun. 2014).

According to qPCR results, *E. necator* spores were present at the beginning of the test in low frequency, and no development has occurred at the later dates. Visual notations in the field confirmed this hypothesis because powdery mildew symptoms were only observed late in the season. The detection with the method according to the invention therefore correlates well with the presence of the fungus and its development on the plants.

Example 5: qPCR Analysis and Powdery Mildew Symptoms Monitoring in Natural Infestation Situations Further tests have been conducted in 2015 in natural infestation conditions in two different regions in France (Champagne region and Armagnac region). In each region, the assays were conducted on several parcels (10 parcels in the Champagne region and 9 parcels in the Armagnac region). For each test, samples of 10 leaves were collected per parcel. Moreover, this amount of samples was collected at three different developmental stages of the grapevine plants: a first sample collection was made at developmental stage BBCH 14/15 (4 to 5 developed leaves), a second sample collection at stage BBCH 53 (6 to 7 developed leaves), and a third sample collection at stage BBCH 57 (8 to 10 developed leaves).

In parallel, the apparition and development of leave symptoms have also been carefully monitored. This monitoring was performed starting 15 days after stage BBCH 14/15, then every 15 days until late developmental stages, including stage BBCH 61 (flowering) and stage BBCH 71 (fruit formation).

One important observation was that, in the parcels of both regions, the qPCR method according to the invention was able to detect *E. necator* very early in the development of the grapevines. In the two regions, it has been possible to detect the presence of *E. necator* as early as the first developmental stage tested, BBCH 14/15, well before any visual symptoms could be observed.

In the Champagne region, the assay also revealed that the development of the disease was progressing in the different parcels (only 3 parcels out of 10 showed the presence of *E. necator* at stage BBCH 14/15, while 8 parcels out of 10 showed it at stage BBCH 57). Moreover, leave symptoms only started to be observable at stage BBCH 57, and then progressed in the different parcels until stage BBCH 71. The assay in the Champagne region however experienced moderate infestation, due to the preventive application of fungicides during the test. This latter observation at least shows that preventive treatments can keep the development of *E. necator* symptoms under control, while the presence of the fungus was observed by qPCR very early on the development of the grapevine.

In the Armagnac region, *E. necator* has also been detected early in some parcels (at BBCH 14/15), but did not show a significant progression in more parcels as the grapevines were developing (only 3 parcels showed detectable amounts of *E. necator* using the qPCR method at stage BBCH 57). This may be explained by the fact that the disease has progressed slowly, possibly due to the climatic conditions during the test, as no visual leaves symptoms could be observed before stage BBCH 61. However, no fungicide treatments occurred on these parcels, and the assay has revealed that the disease has largely developed during the later developmental stages (BBCH 61 and BBCH 71). And interestingly, the parcels that appeared to be the most infested at these late developmental stages were the same ones in which *E. necator* had been detected at earlier stages (BBCH 14/15 and BBCH57) by the qPCR method. These results further demonstrate that the qPCR method according to the invention is an accurate method for detecting *E. necator* in grapevine fields at very early stages in the development of the plants, thereby enabling preventive, but precise, treatments to be applied before the disease can spread and really affect the crop.

The invention claimed is:

1. A method for the specific detection of the fungus *Erysiphe necator*, comprising:
   (a) subjecting a sample to quantitative polymerase chain reaction (qPCR) amplification using a pair of oligonucleotide primers comprising:
      (i) an oligonucleotide consisting of the nucleotide sequence of SEQ ID NO: 1; and
      (ii) an oligonucleotide consisting of the nucleotide sequence of SEQ ID NO: 2, and
   (b) determining the presence, or absence, of *Erysiphe necator* in the sample by visualizing, or not, the target DNA amplified by the qPCR.

2. The method of claim 1, wherein amplification comprises amplifying at least a part of the *Erysiphe necator* Intergenic Transcribed Spacer (ITS) sequence.

3. The method of claim 1, wherein a nonspecific DNA-intercalating dye is used in visualizing, or not, in step (b) the target DNA amplified by the qPCR.

4. The method of claim 3, wherein the non-specific DNA-intercalating dye is the compound N',N'-dimethyl-N-[4-[(E)-(3-methyl-1,3-benzothiazol-2-ylidene)methyl]-1-phenylquinolin-1-ium-2-yl]-N-propylpropane-1,3-diamine.

5. A method for the specific quantification of the fungus *Erysiphe necator*, comprising:
   (a) subjecting a sample to quantitative polymerase chain reaction (qPCR) using a pair of oligonucleotide primers comprising:
      (i) an oligonucleotide consisting of the nucleotide sequence of SEQ ID NO: 1; and
      (ii) an oligonucleotide consisting of the nucleotide sequence of SEQ ID NO: 2, and
   (b) if present, determining the quantity of *Erysiphe necator* in the sample by comparing the measured quantity of target DNA amplified by the qPCR with reference DNA amplification data.

6. The method of claim 5, wherein a nonspecific DNA-intercalating dye is used in determining the measured quantity of target DNA amplified by the qPCR for comparing in step (b).

7. The method of claim 6, wherein the non-specific DNA-intercalating dye is the compound N',N'-dimethyl-N-[4-[(E)-(3-methyl-1,3-benzothiazol-2-ylidene)methyl]-1-phenylquinolin-1-ium-2-yl]-N-propylpropane-1,3-diamine.

8. A method for the specific detection of the fungus Erysiphe necator, comprising:
   (a) subjecting a sample to quantitative polymerase chain reaction (qPCR) amplification using the pair of oligonucleotides consisting of nucleotide sequences SEQ ID NO: 1 for the forward primer and SEQ ID NO: 2 for the reverse primer; and
   (b) determining the presence, or absence, of *Erysiphe necator* in the sample by visualizing, or not, the target DNA amplified by the qPCR,
   wherein the determination of the presence of *Erysiphe necator* in the sample is made with an oligonucleotide probe selected from the group consisting of:
      (i) the oligonucleotide having nucleotide sequence SEQ ID NO: 6;
      (ii) the oligonucleotide having nucleotide sequence complementary to nucleotide sequence SEQ ID NO: 6; and
      ii) any oligonucleotide having a nucleotide sequence of at least 10 contiguous nucleotides of the oligonucleotides in (i) and (ii), with the exception of the specific oligonucleotide having the nucleotide sequence cgtagagccca (SEQ ID NO: 9).

9. The method of claim 8, wherein the oligonucleotide probe is selected from the group consisting of:
   (i) the oligonucleotide having the nucleotide sequence SEQ ID NO: 6; and
   (ii) the oligonucleotide having the nucleotide sequence complementary to the nucleotide sequence SEQ ID NO: 6.

10. The method of claim 8, wherein a nonspecific DNA-intercalating dye is used in determining the measured quantity of target DNA amplified by the qPCR for comparing in step (b).

11. The method of claim 10, wherein the non-specific DNA-intercalating dye is the compound N',N'-dimethyl-N-[4-[(E)-(3-methyl-1,3-benzothiazol-2-ylidene)methyl]-1-phenylquinolin-1-ium-2-yl]-N-propylpropane-1,3-diamine.

12. A diagnostic kit used in detecting and/or quantifying the fungus *Erysiphe necator*, comprising a pair of oligonucleotides consisting of nucleotide sequences SEQ ID NO: 1 for the forward primer and SEQ ID NO: 2 for the reverse primer, and a nonspecific DNA-intercalating dye.

13. The diagnostic kit according to claim 12, wherein the non-specific DNA-intercalating dye is the compound N',N'-dimethyl-N-[4-[(E)-(3-methyl-1,3-benzothiazol-2-ylidene) methyl]-1-phenylquinolin-1-ium-2-yl]-N-propylpropane-1,3-diamine.

* * * * *